United States Patent
Nguyen et al.

(10) Patent No.: US 10,881,702 B2
(45) Date of Patent: Jan. 5, 2021

(54) CELASTROL AND DERIVATIVES THEREOF FOR THE TREATMENT OF TUMOURS AND PRECANCEROUS DISEASES OF THE SKIN

(71) Applicant: PIERRE FABRE MEDICAMENT, Boulogne-Billancourt (FR)

(72) Inventors: Thien Nguyen, Rouffiac-Tolosan (FR); Arnaud Pillon, Saint Orens de Gameville (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 197 days.

(21) Appl. No.: 15/998,967

(22) PCT Filed: Feb. 17, 2017

(86) PCT No.: PCT/EP2017/053596
§ 371 (c)(1),
(2) Date: Aug. 17, 2018

(87) PCT Pub. No.: WO2017/140834
PCT Pub. Date: Aug. 24, 2017

(65) Prior Publication Data
US 2020/0138888 A1 May 7, 2020

(30) Foreign Application Priority Data
Feb. 17, 2016 (FR) .................................... 16 51279

(51) Int. Cl.
| | |
|---|---|
| *A61K 36/37* | (2006.01) |
| *A61P 35/00* | (2006.01) |
| *A61K 31/122* | (2006.01) |
| *A61K 31/215* | (2006.01) |

(52) U.S. Cl.
CPC ............ *A61K 36/37* (2013.01); *A61K 31/122* (2013.01); *A61K 31/215* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 2009/0054438 A1* | 2/2009 | Ronai | ..................... | C07J 63/008 514/237.5 |
| 2011/0263693 A1* | 10/2011 | Vinson-Hieronymus | ..................... | A61P 35/02 514/453 |
| 2015/0004696 A1* | 1/2015 | Tiedemann | ........ | C07K 14/4738 435/375 |
| 2019/0134128 A1* | 5/2019 | Nguyen | ................. | A61K 36/37 |

FOREIGN PATENT DOCUMENTS

| | | |
|---|---|---|
| WO | WO 2007/117466 A3 | 10/2007 |
| WO | WO 2007/117486 A2 | 10/2007 |
| WO | WO 2009/026163 A1 | 2/2009 |

OTHER PUBLICATIONS

Cascao R. et al. Celastrol: A Spectrum of Treatment Opportunities in Chronic Diseases. Frontiers in Medicine vol. 4 Article 69, Jun. 1-18, 2017. (Year: 2017).*
Abbas et al., "Preclinical Studies of Celastrol and Acetyl Isogambogic Acid in Melanoma", Clin Cancer Res, XP002762527, vol. 13(22), Nov. 15, 2007, 6769-6778(10pages).
Brinker et al., "Medicinal chemistry and pharmacology of genus Tripterygium (Celastraceae)", Phytochemistry, vol. 68, 2007, pp. 732-766 (35 pages).
Camelio et al., "Total Synthesis of Celastrol, Development of a Platform to Access Celastoid Natural Products", J. Am. Chem. Soc., vol. 137, 2015, pp. 11864-11867(4 pages).
Chen et al., "Formulation, charecterization, and evaluation of in vitro skim permeation and in vivo pharmacodynamics of surface-charged tripterine-loaded nanostructured lipid carriers", International Journal of Nanomedicine, XP002762528, vol. 7, 2012, pp. 3023-3033 (11 pages).
Coppede et al., "Cell cultures of Maytenus licifolia Mart. are richer sources of quinone-methide triterpenoids than plant roots in natura", Plant Cell Tiss Organ Cult, vol. 118, 2014, pp. 33-43(11pages).
Hansen et al., "III. Independent Calculation of the Parameter Components", Journal of Paint Technology, vol. 39, No. 511, Aug. 1967, pp. 511-514 (4 pages).
International Search Report (Form PCT/ISA/210), dated Mar. 17, 2017, for International Application No. PCT/EP2017/053596.
Kannaiyan et al., "Molecular targets of celastrol derived from Thunder of God Vine: Potential role in the treatment of inflammatory disorders and cancer", Cancer Letters, vol. 303, 2011, pp. 9-20(12 pages).
Luo et al., "Antifungal properties of pristimerin and celestrol isolated from Celastrus hypoleucus", Pest Manag Sci, vol. 61, 2005, pp. 85-90 (6 pages).
Marquito Munhoz, "Avaliação do fator de proteção acrescidos com extractos da flora brasileira ricos ern substâncias fenólicas", Rev Ciéne Farm Básìca Apl., XP-002762529, vol. 33, 2012, pp. 225-232(8 pages), with english abstract.
Morita et al., "Antimitotic quinoid triterpenes from Maytenus chuchuhuasca", Bioorganic & Medicinal Chemistry Letters, vol. 18, 2008, pp. 1050-1052 (3 pages).
Sattar et al., "Quinone-Methide Triterpenes From Tissue Cultures of Catha Edulis", Saudi Pharmaceutica Journal, XP008078000, vol. 6, No. 3-4, Jul.-Oct. 1998, pp. 242-245 (4 pages).
Tang et al., "Design and synthesis of celastrol derivatives as anticancer agents", European Journal of Medicinal Chemistry, vol. 95, 2015, pp. 166-173 (8 pages).

* cited by examiner

*Primary Examiner* — Ralph J Gitomer
(74) *Attorney, Agent, or Firm* — Birch, Stewart, Kolasch & Birch, LLP

(57) ABSTRACT

The invention relates to a compound selected from among celastrol, the derivatives thereof and the pharmaceutically acceptable salts of celastrol and its derivatives, or a composition comprising such a compound for use in the topical prevention and/or treatment of a tumour or precancerous disease of the skin.

7 Claims, 2 Drawing Sheets

Figure 1:
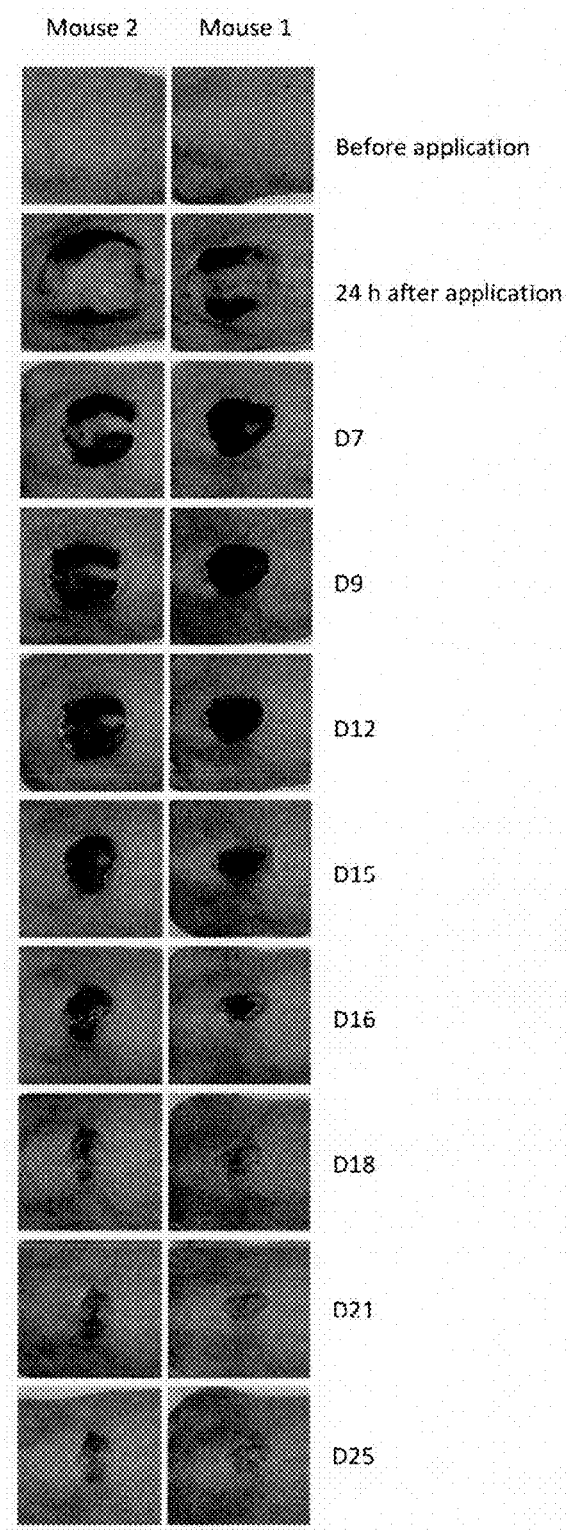

CELASTROL AND DERIVATIVES THEREOF FOR THE TREATMENT OF TUMOURS AND PRECANCEROUS DISEASES OF THE SKIN

The present invention concerns a triterpene, celastrol, also called tripterine, and its derivatives and their pharmaceutically acceptable salts for use in the topical treatment and prevention of tumours and precancerous diseases of the skin.

Tumours and precancerous diseases of the skin are a serious public health problem. A number of these are caused by frequent exposure to UV radiation and can develop into deadly forms of cancer. There are essentially two types of skin tumours:

1) Carcinomas develop from epidermal cells, either from the basal layer (basal cell carcinoma), or from the upper layers (squamous cell carcinoma). They are the most frequent, accounting for 90% of skin cancers, with 75% of these being basal cell carcinoma and 20% squamous cell carcinoma. Basal cell carcinomas never develop metastases; squamous cell carcinomas do so infrequently, mainly in the lymph nodes close to the tumour. Cancers generally develop in several stages. For squamous cell carcinomas, the tumour often begins as a localized lesion in the epidermis. A crust (actinic keratosis) or a kind of eczema (Bowen's disease) forms on the surface. It is the invasion of the deeper dermis that characterises the invasive carcinoma stage.

2) Melanomas develop from melanocytes, the cells that produce melanin, which is responsible for the brown or red pigmentation of the skin. Indeed, there are two main types of pigments: brown ones, which confer tanning and a certain protection against UV, and red ones (fair skin) which do not protect. Individuals who produce mainly red pigments do not tan and are therefore at higher risk of skin cancer. Melanocytes are normally present in the epidermis, associated with epidermal cells in the deep part of the skin. The "beauty spot", or nevus, is a benign lesion corresponding to an accumulation of melanocytes in the dermis, which explains its brown or red colour. Melanomas are much rarer, but can develop in the young. They must be detected and treated quickly because they can spread throughout the body and produce metastases that are very difficult to treat.

Actinic keratosis (AK), also called solar keratosis, is a dermatological pathology. It is a hypertrophy of the stratum corneum of the epidermis. AK is the first stage leading to the development of squamous cell carcinoma and is therefore regarded as a "precancerous" lesion. Although the vast majority of AKs are benign, some studies report that about 10% can transform into squamous cell carcinoma. Between 40% and 60% of squamous cell skin cancers come from untreated AKs. Roughly 2% to 10% of squamous cell skin cancers spread to internal organs and are life-threatening.

AK occurs in areas of the body frequently exposed to the sun (especially UV-B radiation). This mainly affects the Caucasian population. For example, the prevalence of actinic keratosis in Australia is estimated at about 40%. In the United States, it is estimated that more than 8.2 million patients have AK. The estimated annual cost to treat AK in the United States is about US$1 billion in 2002.

There are various therapeutic approaches for treating AK: cryotherapy, surgery, topical photodynamic therapy (PDT), laser, curettage and electrocoagulation, topical applications containing imiquimod, 5-fluorouracil, ingenol mebutate or diclofenac. The treatment must be adapted decoding to the location of the AK and its features.

However, these various treatments are sometimes unsuccessful, some are poorly tolerated by patients and some can leave irreversible and unsightly marks. Therefore, there is still a genuine need for alternative, effective, well-tolerated and rapid treatments for AK.

Celastrol (CLS) of formula (I) below and its derivatives, notably of the quinone-methide triterpene type, including pristimerin of formula (II) below and 22β-hydroxytingenone of formula (III) below, are molecules extracted from plants of the Celastraceae family, in particular from the roots of *Maytenus ilicifolia* or *Tripterygium hypoglaucum* but also *Triptetygium wilfordii* or Lei gong teng, the best known in terms of use in traditional Chinese medicine.

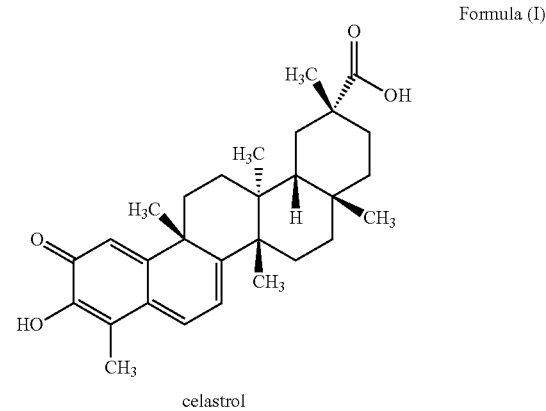

Formula (I)

celastrol

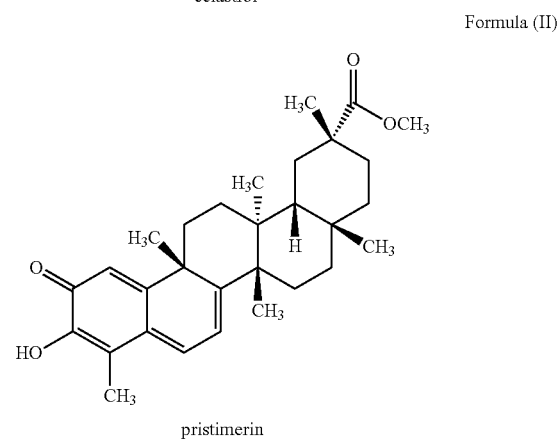

Formula (II)

pristimerin

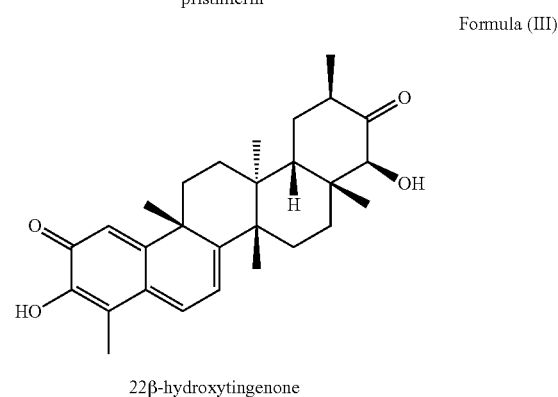

Formula (III)

22β-hydroxytingenone

Extractions of celastrol and its derivatives from the plant roots are often tedious, costly and incompatible with sustainable development because the methods are destructive. Total chemical synthesis has also been described (Camelio et al. JACS 2015, 137, 11864-867). The alternative solution has been to carry out suspension cell cultures of stem cells generated from the roots or leaves of the plant. Recently, Coppede et al. (Plant Cell Tiss Organ Cult 2014; 118:33-43) was able to obtain a significant amount of celastrol (0.304 mg/g of dry cells, maximum concentration obtained after 8 days of culture) from culture of *M. ilicifolia* cells over 10 years of age, i.e., more than 8.85 times that of the plant extraction method.

The inventors have surprisingly shown the efficacy of celastrol in the prevention and treatment of tumours or precancerous diseases of the skin, in particular actinic keratosis or squamous cell carcinoma (SCC).

The present invention thus relates to a compound selected from celastrol and its derivatives, notably pristimerin, the pharmaceutically acceptable salts of celastrol and its derivatives, and mixtures thereof for use in the topical treatment and/or prevention of a tumour or precancerous disease of the skin.

The present invention further relates to a topical composition including at least one compound of the invention, and at least one pharmaceutically acceptable excipient for use in the treatment and/or prevention of a tumour or precancerous disease of the skin.

The present invention further relates to a method for treating and/or preventing a tumour or precancerous disease of the skin by topical administration to a patient in need thereof of an effective amount of a compound or a composition of the invention.

The present invention further relates to the use of a compound or a composition of the invention for the manufacture of a topical medicament for treating and/or preventing tumours or precancerous diseases of the skin.

In the present invention, "pharmaceutically acceptable" means that which is useful in the preparation of a pharmaceutical composition which is generally safe, nontoxic and neither biologically nor otherwise undesirable and which is acceptable for both veterinary and human pharmaceutical use.

"Pharmaceutically acceptable salt" of a compound means a salt that is pharmaceutically acceptable, as defined herein, and that has the desired pharmacological activity of the parent compound.

Pharmaceutically acceptable salts include in particular:

(1) pharmaceutically acceptable acid addition salts formed with pharmaceutically acceptable inorganic acids such as hydrochloric acid, hydrobromic acid, sulfuric acid, nitric acid, phosphoric acid and the like; or formed with pharmaceutically acceptable organic acids such as acetic acid, benzenesulfonic acid, benzoic acid, camphorsulphonic acid, citric acid, ethane-sulfonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and the like, and (2) pharmaceutically acceptable base addition salts formed when an acidic proton present in the parent compound is either replaced by a metal ion, for example an alkali metal ion, an alkaline earth metal ion or an aluminium ion; or coordinated with a pharmaceutically acceptable organic base such as diethanolamine, ethanolamine, N-methylglucamine, triethanolamine, tromethamine and the like; or with a pharmaceutically acceptable inorganic base such as aluminium hydroxide, calcium hydroxide, potassium hydroxide, sodium carbonate, sodium hydroxide and the like.

It may be a sodium salt when the compound has an acid function.

According to the invention, "derivative of celastrol" means all derivatives of celastrol having an efficacy equivalent or superior to celastrol. The efficacy of celastrol and its derivatives can be measured by evaluating their effect on the variation in the number of actinic keratosis lesions during an efficacy test such as the one presented in the examples below. "Equivalent efficacy" means that the derivative of celastrol will have an efficacy between 50% and 100%, preferentially between 80% and 100% of that of celastrol. Therefore, "equivalent or superior efficacy" means that the derivative of celastrol will have an efficacy greater than or equal to 50%, preferentially 80%, of that of celastrol.

In an embodiment, the derivatives of celastrol are active terpenoid metabolites such as those cited in Brinker et al. (2007) Phytochemistry 68:732-766; Tang W J et al. Eur J Med Chem 2015, 95:166-173; Luo D Q et al. Pest Manag Sci 2005, 61(1):85-90; and Morita H et al. Bioorg & Med Chem Let 2008, 18:1050-52. The derivative of celastrol may be pristimerin or 22β-hydroxytingenone. Preferentially, the derivative of celastrol will be pristimerin.

In another embodiment the compound of the invention is selected from the group including or consisting of celastrol, pristimerin, 22β-hydroxytingenone and one of their pharmaceutically acceptable salts. In another embodiment the compound of the invention is selected from the group including or consisting of celastrol, pristimerin and one of their pharmaceutically acceptable salts. In another embodiment the compound of the invention is celastrol or one of its pharmaceutically acceptable salts.

Celastrol, its derivatives and their pharmaceutically acceptable salts according to the invention can be obtained in all the ways known to the skilled person.

The compositions of the invention may contain celastrol and/or one or more of its derivatives and/or their pharmaceutically acceptable salts in purified form or in the form of extract, which may for example be crude or enriched.

Within the meaning of the present invention, "purified form" means a compound including at least 90% by weight, notably at least 95% by weight, notably at least 99% by weight of celastrol, one of its derivatives or a pharmaceutically acceptable salt thereof. Celastrol can notably be obtained by chemical synthesis as described in Camelio et al. (JACS 2015, 137:11864-867).

In another embodiment, celastrol, its derivatives and their pharmaceutically acceptable salts according to the invention may be in the form of extract after extraction of plants of the Celastraceae family, notably plants such as *Tripterygium wilfordii, Tripterygium regelii, Tripterygium hypoglaucum, Celastrus orbiculatus* or *Maytenus ilicifolia*. This extract may be crude or enriched in celastrol, in one of its derivatives, and/or in one of their pharmaceutically acceptable salts. The extract may then include components (including active components) from the plant other than celastrol, its derivatives and their pharmaceutically acceptable salts. The "crude extract" is the extract obtained directly from the plants. "Enriched extract" notably means an extract in which the amount of celastrol, one of its derivatives and/or one of their pharmaceutically acceptable salts is greater than 30% by weight, notably greater than 50% by weight relative to a crude extract.

The purified, crude or enriched extracts of the invention can be obtained from any part of the plants of the Celastraceae family, notably the roots. Alternatively, they can be obtained by cultures of plant cells from these plants. In the case of plant cell cultures, this extract may notably be obtained from the supernatant, suspension or biomass of said cell cultures (as described in particular by Coppede et al. (Plant Cell Tiss Organ Cult 2014; 118:33-43)).

In an embodiment, the compound of the invention, i.e., celastrol, one of its derivatives or one of their pharmaceutically acceptable salts, is in purified form.

"Tumour or precancerous disease of the skin" means in particular tumours or precancerous diseases of the skin selected from the group including or consisting of UV-induced tumours or precancerous diseases of the skin, cutaneous metastases and T lymphomas, notably UV-induced tumours or precancerous diseases.

In an embodiment the UV-induced tumour or precancerous disease of the skin is notably selected from the group including or consisting of actinic keratosis, basal cell carcinoma, melanoma and squamous cell carcinoma.

In another embodiment the UV-induced precancerous disease of the skin according to the invention is actinic keratosis.

All of these tumours or precancerous diseases of the skin are well known to the person skilled in the art who will easily know how to recognise and differentiate them from one another.

In particular, actinic keratosis can be characterised by the appearance of actinic keratosis lesions. "Actinic keratosis lesion" means hypertrophy of the upper layers of the epidermis resulting in thickening of the stratum corneum. The initial stage is characterised by the appearance of erythematous spots with imprecise boundaries, of variable size (about the centimetre) and with a rough surface. At a more advanced stage, the thickening of the stratum corneum increases (yellow or brownish hyperkeratosis, which bleeds if an attempt is made to detach it). Usually the diagnosis is clinical, but a histological examination (skin biopsy) allows a definitive diagnosis (by the presence of ortho and parakeratotic hyperkeratosis, an atrophic or hyperacanthotic epidermis made of dysplastic keratinocytes with numerous nuclear atypia).

Microscopic lesions, only visible histologically, precede the appearance of macroscopic lesions (visible to the naked eye).

According to the invention, "metastases" means the metastases of cutaneous localisation of any type of tumour, for examples metastases of breast tumours, lung tumours, or melanoma.

According to the present invention, "treatment" means the inhibition of the progression, more particularly the regression, preferentially the disappearance of the tumour or precancerous disease of the skin according to the invention.

According to the present invention, "prevention" means preventing or delaying the appearance of the tumour or precancerous disease of the skin according to the invention.

Treatment or prevention according to the invention means in humans or animals. When the precancerous pathology according to the invention is actinic keratosis, "treatment of actinic keratosis" means in particular the inhibition of the appearance of new actinic keratosis lesions, the inhibition of the progression of existing actinic keratosis lesions (notably from microscopic to macroscopic), the inhibition of the growth of existing macroscopic actinic keratosis lesions, the regression of existing actinic keratosis lesions, and/or the disappearance of existing actinic keratosis lesions.

According to the invention, "topical" means that the compound or the composition of the invention will be administered by application to the surface of the skin or mucous membranes.

The topical composition of the invention may notably be in any form allowing topical application: cream, gel, ointment, patch, etc. Preferentially, the composition of the invention will be in the form of cream.

The topical composition of the invention will preferentially include celastrol, and/or one or more of its derivatives and/or their pharmaceutically acceptable salts and at least one pharmaceutically acceptable excipient.

Celastrol is a very lipophilic molecule, therefore very slightly soluble in water. An in silico simulation with ACD/Labs software version 12.02 (Advance Chemical Development, Inc.) makes it possible to predict its solubility (according to Hansen C. M. J Paint Technol 1967; 39:511). As a function of the pH for example, Hansen et al. indicate that for celastrol solubility increases with pH. Celastrol is thus more soluble in basic medium. The composition of the invention will thus preferentially have a pH higher than 7, preferentially higher than 9.

In an embodiment, the topical composition of the invention includes celastrol and/or one or more of its derivatives and/or their pharmaceutically acceptable salts at a concentration between 0.002% and 20% by weight relative to the weight of the final composition, for example between 0.005% and 5%, notably between 0.25% and 1%.

In another embodiment, the topical composition of the invention includes celastrol or a pharmaceutically acceptable salt at a concentration between 0.002% and 20% by weight relative to the weight of the final composition, for example between 0.005% and 5%, notably between 0.25% and 1%.

In another embodiment celastrol and/or one or more of its derivatives and/or their pharmaceutically acceptable salts is administered at a dose between 3.5 µg and 3.5 mg/cm$^2$ of skin, for example between 150 µg and 3000 µg/cm$^2$, for example between 300 µg and 750 µg/cm$^2$.

The compound or the composition of the invention will be administered one to several times per day, and the duration of the treatment may vary according to the severity of the tumour or precancerous disease of the skin to be treated and will be easily adjustable by the skilled person or the practitioner. In one mode of administration the composition will not be administered more than 1, 2, 3, 4 or 5 times, for example more than 3 times.

According to the invention, "pharmaceutically acceptable excipient" means an excipient that is compatible with the other ingredients of the composition and produces no adverse or allergic effect or other undesirable reaction when administered to an animal or a human.

According to the invention, "excipient" means in particular a vehicle such as PEG 400, DMSO, pentylene glycol, linolenic acid, diethyl adipate, ethyl 3-oxohexanoate, ricinoleic acid, octyldodecanol, linoleic acid, sesame oil, capric/caprylic triglycerides, etc.; one or more surfactants, e.g. macrogols, hydroxy stearates, ethoxylated fatty acid esters, ethoxylated fatty alcohols, etc.; one or more solvents, e.g. octyldodecanol, or propyleneglycol dicaprylocaprate; one or more watersoluble polymers, e.g. PVP, hyaluronic acid or sodium hyaluronate; one or more thickeners, e.g. natural or semi-synthetic gums; one or more gelling agents, e.g. carbomers; one or more mineral fillers, e.g. zinc oxide, talc, or clays; one or more emulsifiers such as cetearyl alcohol; one or more preservatives, e.g. phenoxyethanol; one or more antibacterials; one or more antiseptics; one or more antioxidants, e.g. tocopherol acetate; one or more chelating agents, e.g. EDTA; one or more pigments; one or more fragrances; one or more dyes; one or more pH adjusting agents such as salts, acids, bases; or a mixture thereof.

The present invention is illustrated by the following nonlimiting examples.

EXAMPLES

Apoptosis is a fundamental event in cell development (proliferation). The visualisation of apoptosis and the subsequent healing phenomenon reflects the efficacy of medicaments in the treatment of precancerous and cancerous cells. Picato® (0.015% ingenol mebutate) is a product on the market which is indicated for the treatment of actinic keratosis. Picato® is known to induce cell death by a necrotic effect that rapidly eliminates dead cells, followed by a healing phase. To evaluate the "apoptotic" power of celastrol on skin cells (epidermal keratinocytes), we compared the apoptotic effect induced by the topical application of celastrol compared to that of a product already on the market.

Study in Mice—Cutaneous Reaction on Healthy Skin

1. Materials and Methods 1. 1. Mice

Non-inbred hairless SKH-1 strain mice are most commonly used in preclinical dermatological research. These non-pigmented and immunocompetent mice allow easy manipulation of the skin, application of topical agents, exposure to UV radiation and easy visualisation of the cutaneous response. Wound healing, acute biological photo responses and skin carcinogenesis are well characterised in this mouse strain. In addition, the tumours induced in these mice resemble, at both the molecular and the morphological level, UV-induced malignant skin tumours in humans. In this study on healthy skin, 6- to 8-week-old SKH-1 females (18 to 20 grams; Charles River Laboratories) are treated topically with the various compounds.

1. 2. Products Used

Reference Products, Ingenol Mebutate

Picato® (0.015% ingenol mebutate), used in humans to treat actinic keratosis lesions, was administered topically to the animals (2 to 3 animals per group) for 24 hours under a 19-mm-diameter, i.e., 2.83 cm², occlusive patch (Hill Top Research, USA). The patch is loaded with 200 μL of Picato® cream, i.e. 30 μg of active ingredient. The treated skin area is delimited by tattooing on each mouse and the patch is held on the mouse using Tegaderm™ film and Omnifix® and Elastoplast™ adhesive tape. The occlusive dressing is removed after 24 hours, and the animals are followed clinically for 3 to 4 weeks.

Celastrol

Celastrol (Euromedex) is formulated in a vehicle consisting of 5% DMSO-70% glycerol-25% water. The pH is adjusted by adding soda to around 8-8.5 in order to completely solubilise the powder. The initial concentration is 10 mg/mL then serial dilutions in the vehicle yield concentrations of 5 and 2.5 mg/mL. Celastrol is applied topically for 30 hours under a 19-mm-diameter occlusive patch. The patches are loaded with 200 μL of the various celastrol solutions, i.e. 2000 μg, 1000 μg or 500 μg of active ingredient.

As placebo control, an additional group is treated with 200 μL of vehicle alone.

The treated skin area is delimited by tattooing on each mouse and the patch is held on the mouse using Tegaderm™ film and Omnifix® and Elastoplast™ adhesive tape. The occlusive bandage is removed after 30 hours and the animals are followed clinically for 3 to 4 weeks.

1. 3. Evaluation of the Cutaneous Reaction to the Treatments

Clinical Monitoring

The animals are weighed twice per week. The treated area of each animal is photographed two to three times per week in order to follow the progression of the cutaneous reaction and healing.

2. Results 2.1 Clinical Monitoring

The topical treatments are well tolerated: Picato® and celastrol have no effect on the weight of SKH-1 mice. The treated mice developed in the same way as those that received the vehicle alone. This indicates that these products, via this route of administration and at the doses used, are extremely well tolerated by the animals and that there is therefore no systemic toxicity.

2.2. Cutaneous Reactions to the Treatments

Study 1: Effect of Ingenol Mebutate on Healthy Skin

A cutaneous reaction to the ingenol mebutate treatment is visible on the skin of the treated mice as of day 2, i.e. 24 hours after discontinuation of the occlusive treatment (FIG. 1). This reaction is manifested by a central phlyctene, inflammatory redness and haemorrhagic zones at the margins of the treated area. The entire lesioned area becomes necrotic on day 7, which reflects high cell death activity (apoptosis induced by the product). The cutaneous reaction appears deep and the dermal and hypodermal layers are affected. A crust forms, followed by reepithelialisation from the wound edges (on day 12-15). The crust is then resorbed on day 21 and healing continues (scar maturation phase).

Study 2: Effect of Velastrol on Healthy Skin

Figure 2:
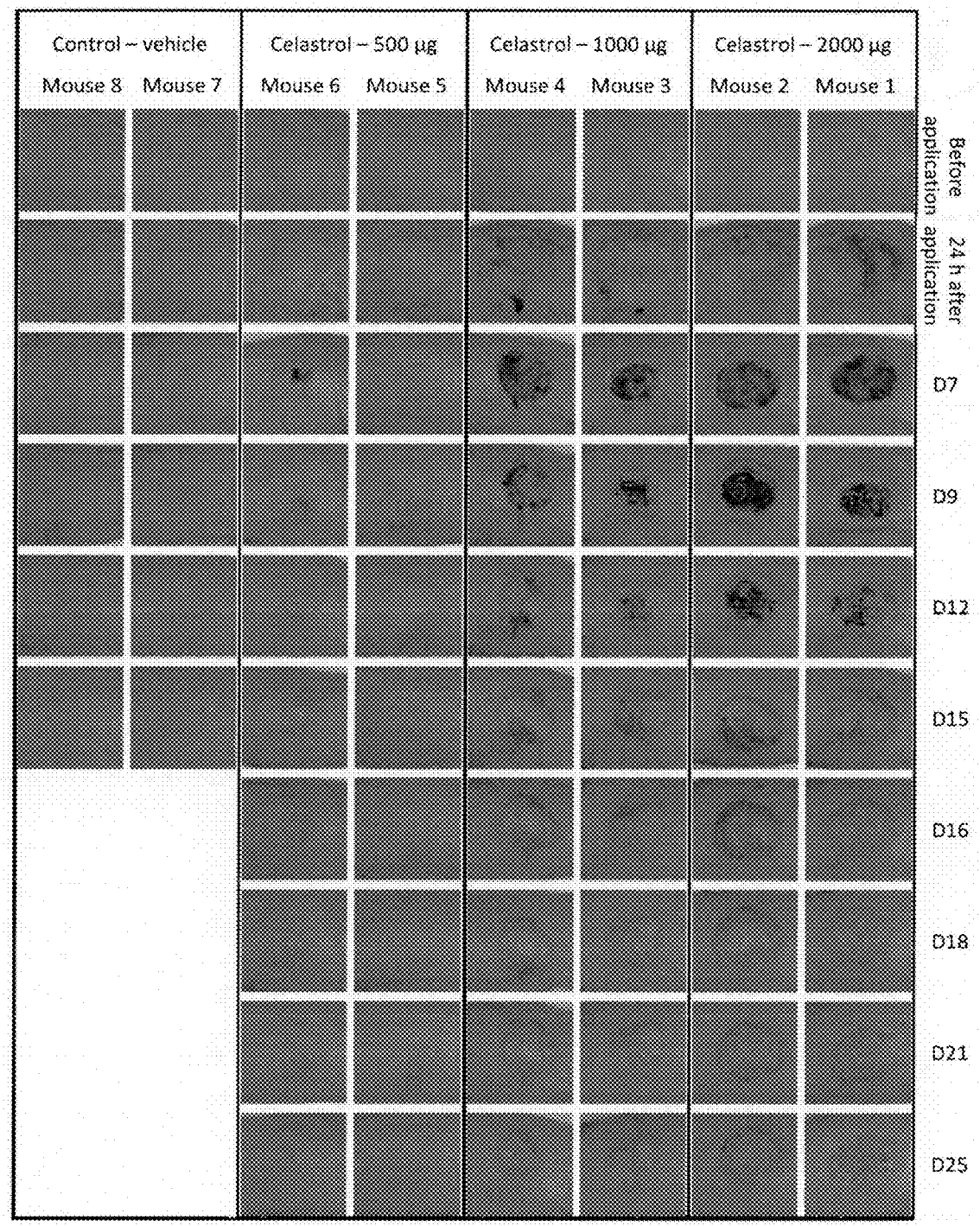

A cutaneous reaction to the celastrol treatment is visible on the skin of the treated mice as of day 3, i.e. 24 hours after discontinuation of the occlusive treatment (FIG. 2). This dose-dependent reaction is manifested by a central phlyctene and inflammatory redness. Unlike Picato®, no haemorrhagic zones are observed even at the highest dose and the pro-apoptotic action of celastrol seems localised in the epidermis and remains superficial. The healing process starts on day 7 in a dose-dependent manner; the skin regains an almost normal appearance a few days later. A slight hypertrophy of the scar area remains on day 28 for the 1000 μg and 2000 μg doses. The vehicle alone has no effect on the skin of SKH-1 mice.

Surprisingly, it was thus shown that, on the application area of the mouse skin, celastrol induces in vivo the apoptosis of epidermal cells in a dose-dependent manner (starting at 500 μg/application), as also observed with Picato®. Moreover, in mice treated with celastrol, about one week after the apoptosis phase, cutaneous repair by scarring is observed, and the skin regains an almost normal appearance a few days later. This is the first time that the in vivo apoptotic effect of celastrol has been shown in animals under topical application. Celastrol thus exhibits all the essential characteristics for an effective treatment of precancerous and cancerous diseases, notably actinic keratosis: death of precancerous or cancerous cells, regeneration of new cells to return to the situation of healthy skin.

FIGURE LEGENDS

FIG. 1: Photographs of the skin of SKH-1 mice treated with Picato® (0.015% ingenol mebutate). The occlusive topical dressing is maintained for 24 hours and the progression of the cutaneous reaction is then followed over time.

FIG. 2: Photographs of the skin of SKH-1 mice treated topically with celastrol (2000 μg, 1000 μg and 500

μg/mouse, the representative mice 1&2, 3&4 and 5&6, respectively). The placebo control group is treated with the vehicle alone (mice 7&8). The occlusive dressing is maintained for 30 hours and the progression of the cutaneous reaction is then followed over time.

The invention claimed is:

1. A method for a topical treatment of actinic keratosis, comprising administering to a patient in need thereof an effective amount of a compound selected from celastrol, pristimerin, 22β-hydroxytingenone and a pharmaceutically acceptable salt thereof.

2. A method for a topical treatment of actinic keratosis, comprising administering to a patient in need thereof an effective amount of a topical composition comprising one or more compound(s) selected from celastrol, pristimerin, 22β-hydroxytingenone and a pharmaceutically acceptable salt thereof, and at least one pharmaceutically acceptable excipient.

3. The method according to claim 2, wherein the compound is celastrol or a pharmaceutically acceptable salt thereof.

4. The method according to claim 2, wherein the compound(s) is/are present in an extract obtained from a plant of the Celastraceae family.

5. The method according to claim 2, wherein the compound(s) is/are present at a concentration between 0.002% and 20% by weight relative to the weight of the final composition.

6. The method according to claim 2, wherein the compound(s) is/are administered at a dose between 3.5 μg/cm$^2$ and 3.5 mg/cm$^2$ of skin.

7. The method according to claim 1, wherein the compound is celastrol or a pharmaceutically acceptable salt thereof.

* * * * *